United States Patent [19]

Huebner

[11] Patent Number: 5,697,934

[45] Date of Patent: Dec. 16, 1997

[54] TENSION BAND WIRING PIN AND METHOD

[76] Inventor: Randall J. Huebner, 18650 SW. Hart Rd., Aloha, Oreg. 97005

[21] Appl. No.: 759,075

[22] Filed: Dec. 2, 1996

[51] Int. Cl.$^6$ ...................................................... A61B 17/58
[52] U.S. Cl. .............................. 606/103; 606/59; 606/60; 606/72; 606/74
[58] Field of Search ..................... 606/72, 73, 74, 606/103, 62, 64, 67; D8/367; 411/484, 489, 507, 400

[56] References Cited

U.S. PATENT DOCUMENTS

| | | | |
|---|---|---|---|
| 464,465 | 12/1891 | Rogers | 411/400 |
| 2,267,925 | 12/1941 | Johnston . | |
| 2,579,968 | 12/1951 | Rush . | |
| 3,351,054 | 11/1967 | Florek . | |
| 4,146,022 | 3/1979 | Johnson et al. | 606/103 |
| 4,169,470 | 10/1979 | Ender et al. . | |
| 4,483,335 | 11/1984 | Tornier | 606/64 |
| 4,506,662 | 3/1985 | Anapliotis . | |
| 4,667,663 | 5/1987 | Miyata . | |
| 4,852,559 | 8/1989 | Chernoff . | |
| 5,330,476 | 7/1994 | Hiot et al. . | |
| 5,486,174 | 1/1996 | Fournet-Fayard et al. | 606/73 |
| 5,499,983 | 3/1996 | Hughes | 606/73 |

*Primary Examiner*—Gary Jackson
*Assistant Examiner*—Julian W. Woo
*Attorney, Agent, or Firm*—Kolisch, Hartwell, Dickinson, McCormack & Heuser

[57] ABSTRACT

A bone pin for use in repair of a bone fracture in conjunction with a tension band wire. The pin includes an elongate shaft with a leading end and a trailing end with the leading end being configured to be inserted into a bone on a first side of a fracture and across the fracture. The pin further includes a retaining band with a first end seamlessly joined to the shaft at a first point on the trailing end of the shaft and extending in a radially outward direction therefrom and a second end seamlessly joined to the shaft at a second point on the trailing end of the shaft and extending in a radially outward direction therefrom. The band further includes a middle region extending in a generally arcuate course between the first and second ends to form a closed seamless loop at the trailing end of the shaft with the loop being sized to receive a tension band wire and retain the wire in a position at least partially overlying the trailing end of the shaft.

25 Claims, 2 Drawing Sheets

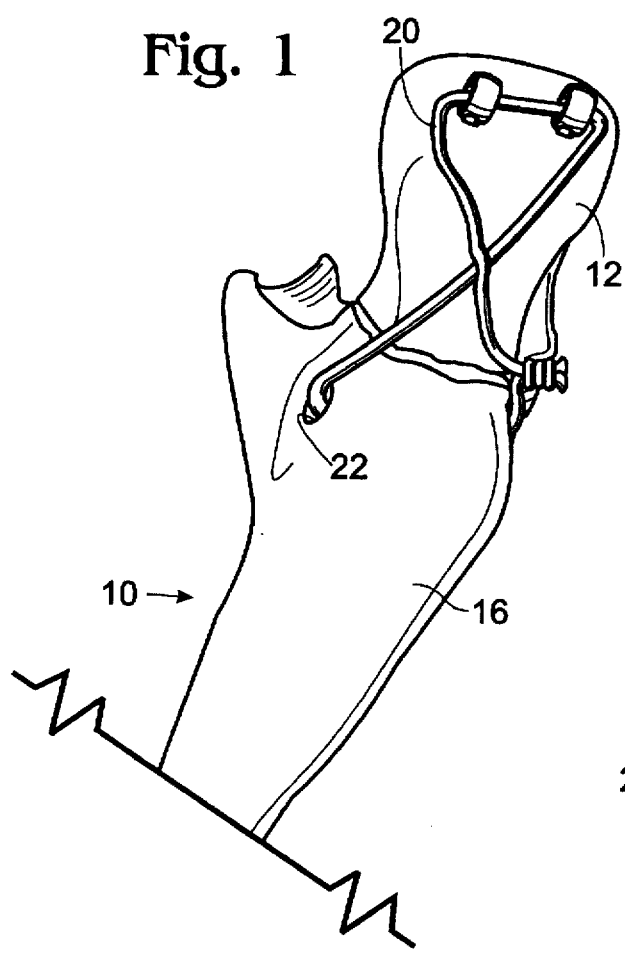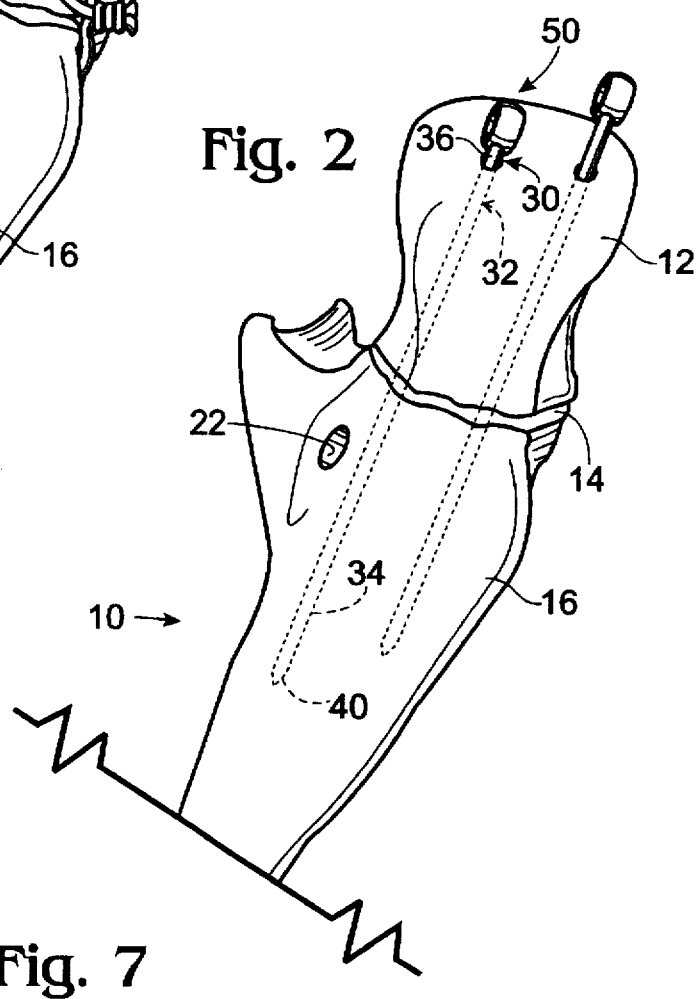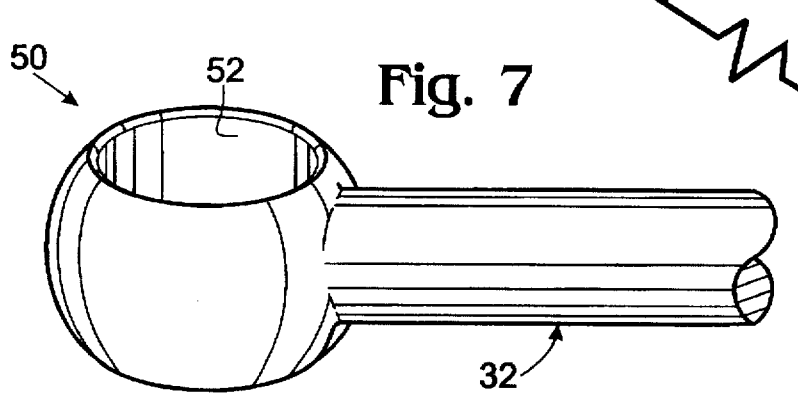

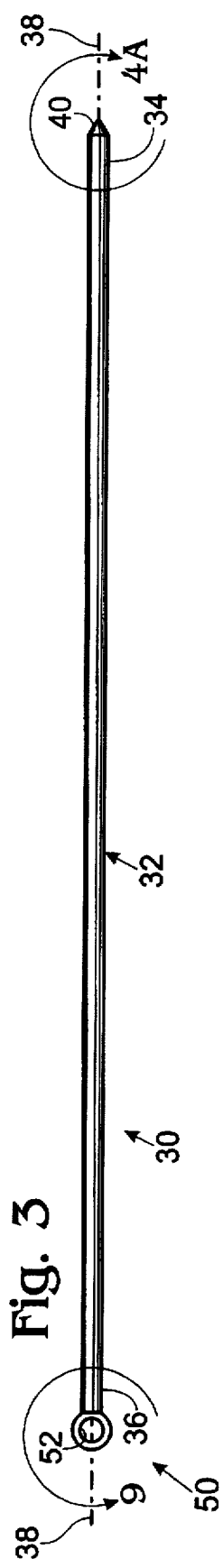
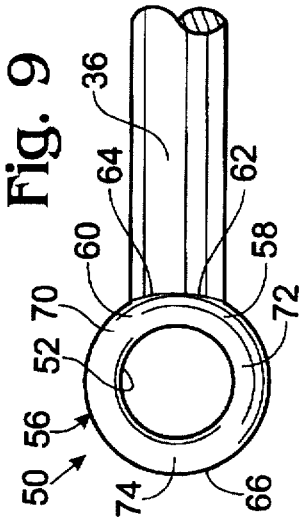
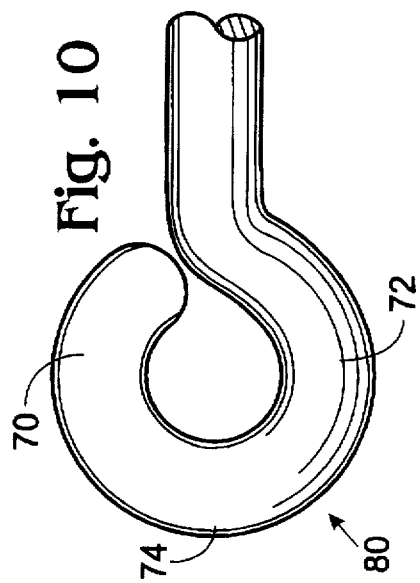
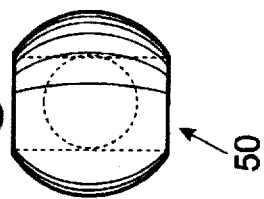
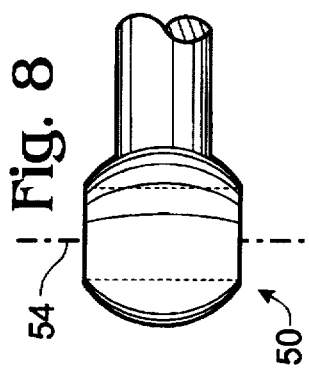
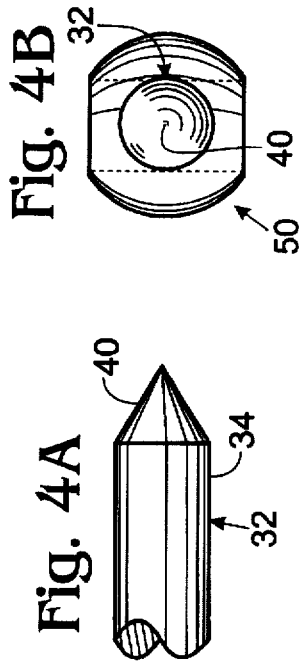
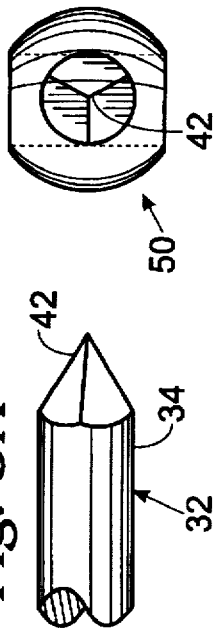

TENSION BAND WIRING PIN AND METHOD

FIELD OF THE INVENTION

The present invention relates generally to repair of bone fractures. More particularly, it is directed to a bone pin and method of using the same for use with tension band wire treatment of bone fractures.

BACKGROUND OF THE INVENTION

Tension band wiring is a well-known technique for repairing bone fractures in which a section of flexible wire is used to wire together two bone fragments. In one form of this technique, a hole is formed in each fragment and the wire is looped through each hole, generally in the path of a figure eight. In another form, typically involving a fracture at an end of a bone, one of the ends of the figure eight is simply looped around the end of the bone. In this form, the end of the wire looped over the end of the bone is generally held in place with stiff stabilizing wire that has a hook formed at one end. The end of the wire without the hook is driven into the bone and when the hook end reaches the bone it is driven in over the wire, somewhat like a staple with one long leg. This prevents the wire from shifting off the end of the bone.

Fractures of the olecranon is one type of fracture that is frequently treated using tension band wiring. In this fracture the stabilizing wires, known as Kirschner wires, are driven through the proximal end of the olecranon into the ulna. The Kirschner wires essentially nail the fracture together. The trailing ends of the wires are bent into U-shaped heads which are driven into the olecranon to capture one end of a tension band. The tension band loops from the proximal end of the olecranon under the ulna and through a hole formed in the ulna on the distal side of the fracture. The tension band keeps the fractured bone segments from separating and the Kirschner wires prevent lateral shifting and torsional rotation.

Unfortunately, in olecranon fractures, as well as others, the tension band frequently causes the stabilizing wire to back out of the hole. This can release the captured tension band thereby destabilizing fracture reduction. Even if the tension band remains captured, the projecting wire can cause irritation or damage in the surrounding tissue. When the stabilizing wires back out, the surgeon typically has to operate to replace or remove the stabilizing wires and/or tension band.

U.S. Pat. No. 4,852,559 to Chernoff discloses a device for pinning bone fractures that addresses some of these problems. In particular, the Chernoff device includes an elongate metal pin with an arcuate hook formed at one end, commonly referred to as a Rush pin. An element extends across the inside of the hook to provide a closed loop. The tension band wire is fed through the closed loop and the element extending across the inside of the hook prevents the pin from backing out. Unfortunately, this device has a number of disadvantages. In particular, the small dement is subject to breakage, in which event metal fragments could find their way into an adjacent joint. Moreover, since the arcuate hook is simply a bend at the end of the pin, the diameter of the material of the hook is quite large and projects out from the end of the bone. In addition to the problem of separation described above, inclusion of a second element requires an assembly step during the manufacturing process. Because of the location of the small element in the hook, attaching the element during assembly would also prove difficult.

Due to limitations and problems with the existing devices and methods for retaining tension bands, it is an object of the present invention to provide a simple and reliable method of repairing a fracture using a tension band wire.

Another object is to provide a bone pin for use in repairing a fracture with a tension band wire.

It is another object of the present invention to provide a bone pin for use with a tension band that is formed as a seamless body.

One more object of the present invention is to provide a bone pin for use with tension bands, where the pin does not project significantly above the surface of the bone when installed.

Yet another object of the present invention is to provide a bone pin for use with tension bands that would not separate into loose fragments in the event of failure.

It is also an object of the invention to provide a bone pin for use in repairing a bone fracture with a tension band wire, where the pin retains the wire over its trailing end to prevent the pin from backing out.

SUMMARY OF THE INVENTION

The present invention is a bone pin for use in repair of a bone fracture in conjunction with a tension band wire. The pin includes an elongate shaft with a leading end and a trailing end with the leading end being configured to be inserted into a bone on a first side of a fracture and across the fracture. The pin further includes a retaining band with a first end seamlessly joined to the shaft at a first point on the trailing end of the shaft and extending in a radially outward direction therefrom and a second end seamlessly joined to the shaft at a second point on the trailing end of the shaft and extending in a radially outward direction therefrom. The band further includes a middle region extending in a generally arcuate course between the first and second ends to form a closed seamless loop at the trailing end of the shaft with the loop being sized to receive a tension band wire and retain the wire in a position at least partially overlying the trailing end of the shaft.

The present invention also includes a method for repairing a bone fracture including the step of providing a first stabilizing pin, wherein the pin has an elongate shaft with a leading end and a trailing end, the pin further including a head seamlessly formed on the trailing end of the shaft, where the head includes a hole extending therethrough in a direction generally transverse to the axis of the shaft with the hole having a seamless perimeter forming a closed loop. The pin is inserted into the bone from a first side of the fracture so that the loop is disposed adjacent the surface of the bone on the first side of the fracture with the shaft crossing the fracture and the leading end lying on a second side of the fracture. A tension band wire is fed through the hole in the head of the pin and made into a loop extending from the head of the pin to the second side of the fracture to prevent the first and second sides from separating.

Many other features, advantages and additional objects of the present invention will become manifest to those versed in the art upon making reference to the detailed description which follows and the accompanying sheets of drawings in which preferred embodiments incorporating the principles of this invention are disclosed as illustrative examples only.

BRIEF DESCRIPTION OF THE FIGURES

FIG. 1 is perspective view of a fractured olecranon showing the structure and placement of a tension band wire held in place with bone pins made according to the present invention.

FIG. 2 is a perspective view of a fractured olecranon showing placement of pins prior to installation of a tension band wire.

FIG. 3 is a side view of a bone pin according to the present invention.

FIG. 4A is an enlarged view of a conical tip at the end of the pin of FIG. 3.

FIG. 4B is an end view of the conical tip of the pin of FIG. 3.

FIG. 5A is an enlarged view of an alternative tip for the pin of FIG. 3.

FIG. 5B is an end view of a pin using the tip of FIG. 5A.

FIG. 6 is an end view of the pin of FIG. 3 from the left.

FIG. 7 is a perspective view of a head of the pin of FIG. 3.

FIG. 8 is a view of the head as viewed from above in FIG. 3.

FIG. 9 is an enlarged view of the head region of the pin of FIG. 3.

FIG. 10 is a side view of an alternative head for the pin of FIG. 3.

DETAILED DESCRIPTION OF THE PREFERRED EMBODIMENT

An example of a fractured bone in the form of an olecranon is shown generally at 10 in FIGS. 1 and 2. Bone 10 includes a first side 12, a fracture 14 and a second side 16. A tension band wire 20 is illustrated in FIG. 1 made into a loop and extending between the first and second sides to prevent the sides from separating. During installation at the fracture site and prior to being made into a loop, wire 20 is fed through a hole 22 in the bone on the second side of the fracture. The wire is also looped around the end of the bone on the first side of the fracture to thereby hold the first and second sides of the fracture together.

The portion of the tension band wire looped around the end of the bone is held in place by a pair of stabilizing pins such as pin 30 constructed according to the present invention. Pin 30, which is illustrated in FIG. 3, includes an elongate shaft 32 with a leading end 34, a trailing end 36 and an elongate axis 38 extending therebetween. Leading end 34 is preferably formed with either a conical tip 40, as shown in FIGS. 4A and 4B, or a trocar point 42 as shown in FIGS. 5A and 5B. Shaft 32 is preferably between 20 and 70 millimeters long with 50 being typical. The shaft diameter is preferably between 0.032 and 0.093 inches.

The shaft is configured to be inserted into the bone from the first side of the fracture, extend across the fracture and enter the bone on the second side of the fracture. When the pin is positioned in this fashion, it prevents rotation and lateral movement of the bone fragments, thus stabilizing the fracture. This leaves the tension band wire to prevent longitudinal displacement or separation of the fragments.

The shaft may be inserted into the bone using a mallet, preferably following a predrilled hole to ease insertion. Using trocar point 42, it is also possible to insert the shaft by mounting the pin in a drill and drilling the shaft directly into the bone. This method is beneficial because it reduces the number of steps during installation.

A wire retention region in the form of a head 50 is disposed at the trailing end of shaft 32, as shown in FIGS. 7 and 9. Head 50 is preferably generally spherical in shape and approximately one-eighth of an inch in diameter. A hole 52 is formed through head 50 with a central axis 54 generally transverse to elongate axis 38 of shaft 32. See FIG. 8. Hole 52 is preferably formed with a diameter of approximately one-sixteenth of an inch to receive tension band wire 20 therethrough.

With the preferred dimension, head 50 smoothly tapers down to the perimeter of hole 52, leaving a band 56 of material forming a continuous perimeter around the hole, as shown in FIG. 9. Band 56 has first and second ends 58, 60, respectively which seamlessly join to first and second points 62, 64, respectively, on the trailing end of shaft 32. A middle region 66 extends between ends 58, 60 in a generally arcuate path forming the surface of the head. The result is a closed seamless loop through which the wire passes, thereby holding the wire in position over the trailing end of the shaft.

Head 50 may also be described as including opposed lateral portions 70, 72 disposed on either side of elongate axis 38 at the trailing end of the shaft, as shown in FIG. 10. The tension band wire is received between the opposed lateral portions, which hold the wire in place over the trailing end of the shaft. This prevents the shaft from backing out because of the presence of the overlying wire. An end portion 74 connects the free ends of lateral portions 70, 72 to from a closed unitary loop.

In the preferred embodiment, pin 30 is turned on a lathe or screw machine from a single piece of metal to result in a unitary or seamless body. This eliminates the danger of a component part separating from the pin and entering the joint as can occur in prior art pins.

An alternative embodiment of a retention region according to the present invention is shown generally at 80 in FIG. 10. Retention region 80 is simply formed by bending a portion of the pin into a circle centered over the shaft. Although the loop through which the wire passes in this embodiment is not seamless, the entire pin is formed as an integral or unitary unit. By shaping the loop directly over the trailing end of the shaft, the tension band wire can serve to prevent the pin from backing out of the bone as with the first described embodiment.

Although the invention has been described in the context of repairing a fractured olecranon, the pin is suitable for use in other tension band wire fracture repairs, such as in medial mallcolus or metatarsal fractures.

It will now be clear that an improvement in this art has been provided which accomplishes the objectives set forth above. While the invention has been disclosed in its preferred form, it is to be understood that the specific embodiments which have been depicted and described are not to be considered in a limited sense because there may be other forms which should also be construed to come within the scope of the appended claims.

I claim:

1. A tension band wiring system for use in repair of a bone fracture comprising:

a bone pin including an elongate substantially straight shaft with a leading end and a trailing end, the leading end being configured to be inserted into a bone on a first side of the fracture and across the fracture, the bone pin further including a retaining band with a first end seamlessly joined to the shaft at a first point on the trailing end of the shaft and extending in a radially outward direction therefrom and a second end seamlessly joined to the shaft at a second point on the trailing end of the shaft and extending in a radially outward direction therefrom, the band further including a middle region extending in a generally arcuate course between the first and second ends to form a closed seamless loop at the trailing end of the shaft, the loop being sized to receive the tension band wire and retain the wire in a position at least partially overlying the trailing end of the shaft; and an elongate tension band wire configured to be made into a tension band wire loop extending through the retaining band on a first side of the fracture, across the fracture and to a second side of the fracture, the tension band loop being configured to prevent the sides of the fracture from moving apart.

2. The bone pin according to claim 1, further including a trocar point formed at the leading end of the shaft to facilitate insertion of the shaft into the bone.

3. The bone pin according to claim 1, wherein the loop retains the wire substantially centered over the elongate axis of the shaft.

4. The bone pin according to claim 1, wherein the shaft has a diameter and the band has a radial thickness between the inside of the loop and an outer surface of the loop which is less than the diameter of the shaft.

5. The bone pin according to claim 1, wherein the loop is slightly larger than the tension band wire so that the tension band wire can freely pass therethrough.

6. The bone pin according to claim 5, wherein the loop is approximately 50-percent larger in diameter than the tension band wire.

7. The bone pin according to claim 1, wherein the elongate shaft is between 0.032 and 0.093 inches in diameter.

8. The bone pin according to claim 1, wherein the pin is turned from a single piece of material.

9. A method for repairing a bone fracture comprising the steps of:

providing a first stabilizing pin, wherein the pin has an elongate shaft with a leading end and a trailing end, the pin further including a head seamlessly formed on the trailing end of the shaft, where the head includes a hole extending therethrough in a direction generally transverse to the axis of the shaft with the hole having a seamless perimeter forming a closed loop;

inserting the pin into the bone from a first side of the fracture so that the loop is disposed adjacent the surface of the bone on the first side of the fracture, the shaft crosses the fracture and the leading end lies on a second side of the fracture;

feeding a tension band wire through the hole in the head of the pin;

making the tension band wire into a loop extending from the head of the pin to the second side of the fracture to prevent the first and second sides from separating.

10. The method of claim 9, further including the step of inserting a second stabilizing pin into the bone from the first side of the fracture so that the loop is disposed adjacent the surface of the bone on the first side of the fracture, the shaft crosses the fracture and the leading end lies on the second side of the fracture.

11. The method of claim 9, further including the steps of forming a hole through the bone on the second side of the fracture and passing the tension band wire through the hole in the second side of the bone.

12. The method of claim 9, further including the step of predrilling a hole in the bone to receive the pin.

13. An apparatus for repair of a bone fracture, the apparatus comprising:

an elongate tension band wire configured to be made into a tension band wire loop extending from a first side of the fracture, across the fracture and to a second side of the fracture, the tension band loop being configured to prevent the sides of the fracture from moving apart; and a stabilizing pin including an elongate shaft and a head seamlessly joined to a trailing end of the shaft, the head having a hole extending therethrough with the hole being sized to receive the tension band wire and having a substantially continuous perimeter to thereby prevent removal of the tension band wire from the hole after the tension-band wire is formed into a loop, the hole further having a central axis lying substantially coplanar with, and extending generally transverse to, the elongate axis of the shaft.

14. The apparatus of claim 13, further including a second stabilizing pin.

15. The apparatus of claim 13, wherein the head has a generally spherical outer surface.

16. The apparatus of claim 15, wherein the central axis of the hole substantially intersects the center of the head.

17. The apparatus of claim 16, wherein the hole has a radius, and the head has a radius less than twice the radius of the hole.

18. The apparatus of claim 17, wherein the radius of the head is approximately one-eighth of an inch.

19. The apparatus of claim 13, wherein the elongate shaft has a radius and the head has a radius less than three times the radius of the shaft.

20. The apparatus of claim 13, wherein the radius of the head is approximately twice the radius of the shaft.

21. The apparatus of claim 13, wherein the pin includes a trocar point at the leading end of the shaft.

22. A tension band wiring apparatus for repairing a fracture in a bone comprising:

a tension band pin including an elongate shaft with a leading end and a trailing end, the leading end of the shaft being configured to be inserted in the bone on a first side of the fracture and across the fracture, the tension band pin further including a wire retention region disposed at the trailing end of the shaft, the retention region including opposed lateral portions disposed on either side of the elongate axis of the shaft to receive the tension band wire therebetween and retain the wire in place aligned over the trailing end of the shaft to thereby prevent the shaft from backing out of the bone; and an elongate tension band wire configured to be made into a tension band wire loop to be received by the wire retention region over a first side of the fracture and extend across the fracture to a second side of the fracture, the tension band loop being configured to prevent the sides of the fracture from moving apart.

23. The bone pin according to claim 22, wherein the retention region retains the wire substantially centered over the elongate axis of the shaft.

24. The bone pin according to claim 22, wherein the retention region further includes an end portion extending between and connecting the opposed lateral portions to form a closed loop configured to encircle the wire.

25. The bone pin according to claim 22, wherein the retention region is formed as an extension of the elongate shaft bent into a closed circle substantially centered over the axis of the elongate shaft.

* * * * *